United States Patent [19]

Pless et al.

[11] Patent Number: 4,969,465
[45] Date of Patent: Nov. 13, 1990

[54] CARDIAC THERAPY METHOD

[75] Inventors: Benjamin Pless, Menlo Park; Phillip L. Ball, San Jose; Eric Fain, Menlo Park, all of Calif.

[73] Assignee: Ventritex, Inc., Sunnyvale, Calif.

[21] Appl. No.: 353,967

[22] Filed: May 19, 1989

[51] Int. Cl.$^5$ .............................................. A61N 1/362
[52] U.S. Cl. ............................... 128/419; 128/419 PG
[58] Field of Search ........ 128/419 D, 419 P, 419 PG, 128/702, 705

[56] References Cited

U.S. PATENT DOCUMENTS

| | | | |
|---|---|---|---|
| 3,794,045 | 2/1974 | Thaler | 128/419 PG |
| 3,880,147 | 4/1975 | Gruenke et al. | 128/702 |
| 4,421,114 | 12/1983 | Berkovits et al. | 128/419 PG |
| 4,427,011 | 1/1984 | Spurrell et al. | 128/419 PG |
| 4,475,551 | 10/1984 | Langer et al. | 128/419 D |
| 4,493,325 | 1/1985 | Hartlaub et al. | 128/419 PG |
| 4,750,495 | 6/1988 | Moore et al. | 128/419 PG |
| 4,796,620 | 1/1989 | Imran | 128/706 |
| 4,819,643 | 4/1989 | Menken | 128/419 PG |
| 4,830,006 | 5/1989 | Haluska et al. | 128/419 PG |
| 4,869,252 | 9/1989 | Gilli | 128/419 PG |

Primary Examiner—Lee S. Cohen
Assistant Examiner—Kennedy J. Schaetzle
Attorney, Agent, or Firm—Gerstman & Ellis, Ltd.

[57] ABSTRACT

A cardiac therapy method is disclosed, using an implanted cardiac pulse generator. A patient's heartbeat is sensed and the intervals between heartbeats are averaged. The number of temporary storage bins, in the form of RAM locations, are provided, including a sinus bin, a low rate tachycardia bin, a high rate tachycardia bin, and a fibrillation bin. The storage bin corresponding to the cardiac rhythm band of the determined average heartbeat interval is incremented. A maximum count limit is assigned to each storage bin. When the first bin reaches its maximum count limit, a diagnosis of the patient's cardiac rhythm is provided. Upon detection of a tachycardia, a duration timer is started and the tachycardia is treated in accordance with a programmed routine. If sinus is detected during the predetermined time period, then the duration timer is cleared. If fibrillation is detected during the predetermined time period, then the duration timer is cleared and fibrillation is treated by delivering a high energy shock to the heart.

21 Claims, 5 Drawing Sheets

CARDIAC THERAPY METHOD

RELATED APPLICATION

This application is related to Ser. No. 376,372, filed July 6, 1989 and entitled "Cardiac Therapy Method With Duration Timer."

FIELD OF THE INVENTION

The present invention concerns a novel method of cardiac therapy using an implanted cardiac pacer/defibrillator.

BACKGROUND OF THE INVENTION

Implantable defibrillators are known in the prior art in which the spectrum of heart rates is divided into several distinct bands. Such bands may include normal sinus rhythm, tachycardia and fibrillation.

We have found that it would be extremely useful to divide the spectrum of heart rates into five bands, including bradycardia, normal sinus rhythum, slow tachycardia, fast tachycardia and fibrillation. However, when rhythms occur that have a combination of intervals, i.e., where the rhythm is oscillating around a border between two tachyarrhythmias, the implanted device must decide which arrhythmia is present. Further, the device must detect sinus rhythm when it occurs.

The present invention concerns a combined antitachycardia pacemaker/defibrillator which is implanted to treat potentially lethal arrhythmias. However, antitachycardia pacing can be an unpredictably prolonged therapy, and can result in leaving the patient in jeopardy if more definitive therapy is not used within a short period of time. One solution to this problem would be to severely limit the programability of the antitachycardia pacing feature. However, this is not a desirable solution.

Another potential problem in an automatic tiered therapy defibrillator, is that if a rapid arrhythmia such as a high rate tachycardia or fibrillation is detected, and the associated therapy is delivered, the device must know when to stop delivering the therapy. The device could be programmed to stop delivering therapy when the original detection criteria are no longer met.

Currently available defibrillators have a single rate cutoff. If it is exceeded, therapy is delivered. Normally if the average heart rate is high enough to be considered a tachycardia, an automatic device will provide tachycardia therapy. However, it is possible to have rhythms that have an average tachycardia rate but have an alternating pattern of intervals and should not be treated. These rhythms are sometimes called bigeminal rhythms. An example of a bigeminal rhythm is 600 msec/300 msec/600 msec/300 msec/etc. The average interval is 450 msec. If the tachycardia detection criterion is 500 msec, the device would inappropriately diagnose tachycardia.

Some prior art antitachycardia devices require a sequential number of intervals below the interval criterion for tachycardia. However, this makes it difficult to detect arrhythmias unless the arrhythmia rate is very stable.

It is, therefore, an object of the present invention to provide a method for determining arrhythmia hierarchy in an implanted defibrillator which has a number of distinct bands.

Another object of the present invention provide definitive therapy for patients suffering from tachycardia, using an implanted combined antitachycardia pacemaker/defibrillator.

A further object of the present invention is to utilize an arrhythmia detection method using hysteresis, in which there is one rate cutoff for deciding to deliver therapy and a separate, lower rate cutoff, for deciding to cease giving therapy.

A still further object of the present invention is to provide arrhythmia detection inhibition with low tachycardia rate averages, but interval alternans. In this manner, the system will keep track of the ratio of sinus intervals to tachycardia intervals, and will require more tachycardia intervals than sinus intervals in order for an arrhythmia to be detected. Therefore the presence of a tachycardia can be quickly determined, without inappropriately detecting a bigeminal rhythm as tachycardia.

Other objects and advantages of the present invention will become apparent as the description proceeds.

SUMMARY OF THE INVENTION

In accordance with the present invention, a cardiac therapy method is provided using an implanted cardiac pulse generator. In one embodiment, the method comprises the steps of: sensing a patient's heartbeat; providing storage means including a plurality of temporary storage bins, each of which corresponds to a different cardiac rhythm band; determining the intervals between heartbeats; incrementing the storage bin corresponding to the cardiac rhythm band of the determined heartbeat interval weighted by the current coverage; assigning a maximum count limit to each storage bin; detecting when the first bin reaches its maximum count limit; providing a diagnosis of the patient's cardiac rhythm that is responsive to the first bin to reach its maximum count limit; and initializing the temporary storage bins.

In the illustrative embodiment, the step of providing storage means comprises the step of providing a sinus storage bin, a low rate tachycardia storage bin, a high rate tachycardia storage bin, and a fibrillation storage bin.

The method of an embodiment in accordance with the principles of the present invention also comprises the steps of: sensing a patient's heartbeat; determining the intervals between heartbeats; upon detection of an average tachycardia rate, starting a duration timer to time a pre-determined time period and treating for tachycardia in accordance with a programmed routine; if sinus is detected during the predetermined time period, then clearing the duration timer; if fibrillation is detected during the predetermined time period, then clearing the duration timer and treating for fibrillation; and if tachycardia continues for the predetermined time period, then commencing fibrillation therapy.

In the illustrative embodiment, the step of determining the intervals between heartbeats includes the step of averaging a selected number of heartbeats.

The method of an embodiment of the present invention also comprises the steps of: sensing a patient's heartbeat; determining the intervals between heartbeats; if the heartbeats exceed a first rate, then treating for an arrhythmia; and continuing to treat for an arrhythmia unless the heartbeat rate declines to below a second rate, with the second rate being lower than the first rate. This allows use of a higher arrhythmia detection rate in a tiered defibrillator, without the disadvantage of failing to terminate slower arrhythmias that might result from the therapy.

The method of an embodiment of the present invention also includes the steps of: sensing a patient's heartbeat, determining the intervals between heartbeats; determining the ratio of sinus intervals to arrhythmia intervals; treating for arrhythmia only if the number of arrhythmias exceed the number of sinus intervals notwithstanding that the average of the sinus and arrhythmia intervals is shorter than sinus rhythm. This prevents the system from inappropriately detecting a bigeminal rhythm as an arrhythmia.

A more detailed explanation of the invention is provided in the following description and claims, and as illustrated in the accompanying drawings.

DETAILED DESCRIPTION OF THE ILLUSTRATIVE EMBODIMENT

Figure 1:
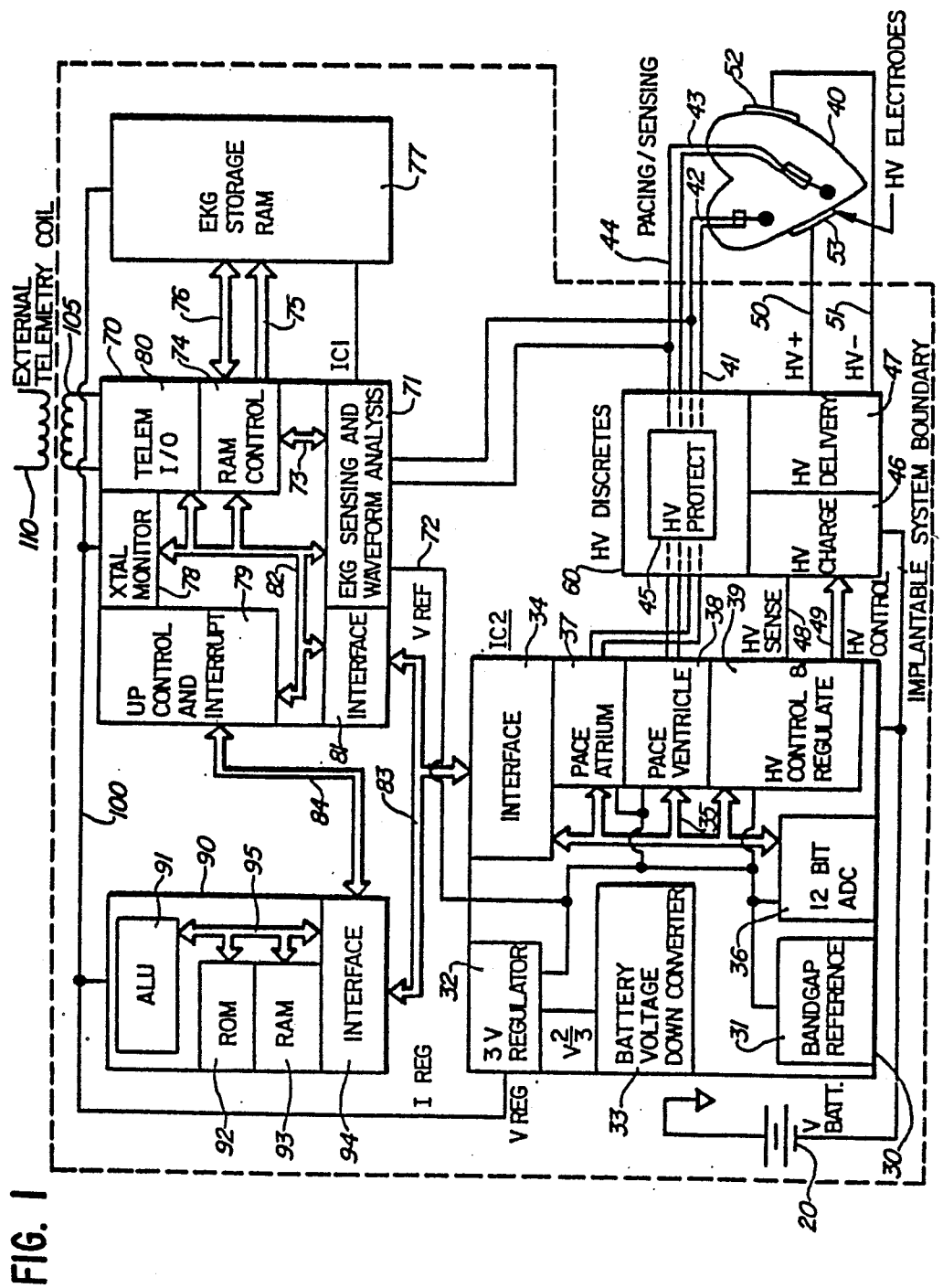
FIG. 1 is a block diagram of an implantable pacer/-defibrillator system constructed in accordance with the principles of the present invention.

Referring to FIG. 1, the block diagram for the implantable defibrillator includes four ICs and a set of high voltage discretes. The battery produces a positive voltage with respect to ground that varies from about 6.4 volts when new, to 5.0 volts at the end of service. The battery directly powers IC2 30 and the high voltage discretes 60.

IC2 contains a band-gap reference circuit 31 that produces 1.235 volts, and 3 volt regulator that powers the microprocessor 90, IC1 70, and the ECG storage RAM 77 through line 100. The 3 volt regulator runs off of a switched capacitor V ⅔ battery voltage down converter 33 for improved efficiency.

The microprocessor 90 communicates with IC2 through a data and address bus 83 and an on-chip interface 34 that contains chip-select, address decoding and data bus logic as is typically used with microprocessor peripherals. The internal bus 35 allows the microprocessor to control a general purpose ADC 36, the atrial pace circuits 37, the ventricular pace circuits 38, and the HV control and regulate block 39.

The ADC 36 is used by the microprocessor to measure the battery and other diagnostic voltages within the device.

The atrial pace circuits 37 include a DAC that provides the ability to pace at regulated voltages. It communicates with the atrium of a heart 40 through two lines. One line 41 is a switchable ground; the other line 42 is the pacing cathode and is also the input to the atrial sense amplifier, as will be described below.

The ventricular pace circuits 37 include a DAC that provides the ability to pace at regulated voltages. It communicates with the ventricle of a heart 40 through two lines. One line 43 is a switchable ground; the other line 44 is the pacing cathode and is also the input to the ventricular sense amplifier, as will be described below.

Both the atrial and ventricular pace lines pass through high voltage protection circuits 45 to keep the defibrillation voltages generated by the device from damaging the pacing circuits 37 and 38.

The HV control and regulate block 39 on IC2 30 is used by the microprocessor 90 to charge a high voltage capacitor included in the HV charge block 46 to a regulated voltage, and then to deliver the defibrillating pulse to the heart 40 through the action of switches in the HV delivery block 47. An HV sense line 48 is used by the HV regulation circuits 39 to monitor the defibrillating voltage during charging. An HV control bus 49 is used by the HV control circuits 39 to control the switches in the HV delivery block 47 for delivering the defibrillating pulse to the electrodes 52, 53 through lines 50 and 51.

IC1 70 is another microprocessor peripheral and provides timing, interrupt, telemetry, ECG storage, and sensing functions.

A dual channel electrogram sensing and waveform analysis section 71 interfaces with the atrium and ventricle of the heart 40 through lines 42 and 44 respectively. The sensed electrogram is amplified and digitized. The amplifiers contained in this section 71 have multiple gain settings that are under microprocessor control for maintaining an AGC. Features such as peak voltage and complex width are extracted by the waveform analysis circuits 71 for the microprocessor 90 to use in discriminating arrhythmias from normal sinus rhythm. The voltage reference 31 from IC2 30 is used by the digitizer circuit 71 in the usual fashion, and is supplied by line 72.

The digitized ECG is provided to the RAM controller 74 through a bus 73. The RAM controller sequences through the addresses of a static RAM 77 to maintain a pretrigger area, and this produces a post trigger area upon command from the microprocessor 90.

The crystal and monitor block 78 has a 100 KHz crystal oscillator that provides clocks to the entire system. The monitor is a conventional R-C oscillator that provides a back-up clock if the crystal should fail.

The microprocessor communicates with IC1 through two buses, 83 and 84. One bus 83 is a conventional data and address bus and goes to an on-chip interface 81 that contains chip select, address decoding and data bus drivers as are typically used with microprocessor peripherals. The other bus 84 is a control bus. It allows the microprocessor to set up a variety of maskable interrupts for events like timer timeouts, and sense events. If an interrupt is not masked, and the corresponding event occurs, and interrupt is sent from IC1 70 to the microprocessor 90 to alert it of the occurrence. On IC1 70, the up control and interrupt section 79 contains microprocessor controllable timers and interrupt logic.

The device can communicate with the outside world through a telemetry interface 80. A coil 105 is used in a conventional fashion to transmit and receive pulsed signals. The telemetry circuits 80 decode an incoming bit stream from an external coil 110 and hold the data for subsequent retrieval by the microprocessor 90. When used for transmitting, the circuit 80 receives data from the microprocessor 90, encodes it, and provide s the timing to pulse the coil 105. The communication function is used to retrieve data from the implanted device, and to change the modality of operation if required.

The microprocessor 90 is of conventional architecture comprising an ALU 91, a ROM 92, a RAM 93, and interface circuits 94. The ROM 92 contains the program code that determines the operation of the device. The RAM 93 is used to modify the operating characteristics of the device as regards modality, pulse widths, pulse amplitudes, and so forth. Diagnostic data is also stored in the RAM for subsequent transmission to the outside world. The Arithmetic Logic Unit (ALU) 91 performs the logical operations directed by the program code in the ROM.

The program code is written to perform certain desirable functions which are best described in flowchart form.

Figure 2:
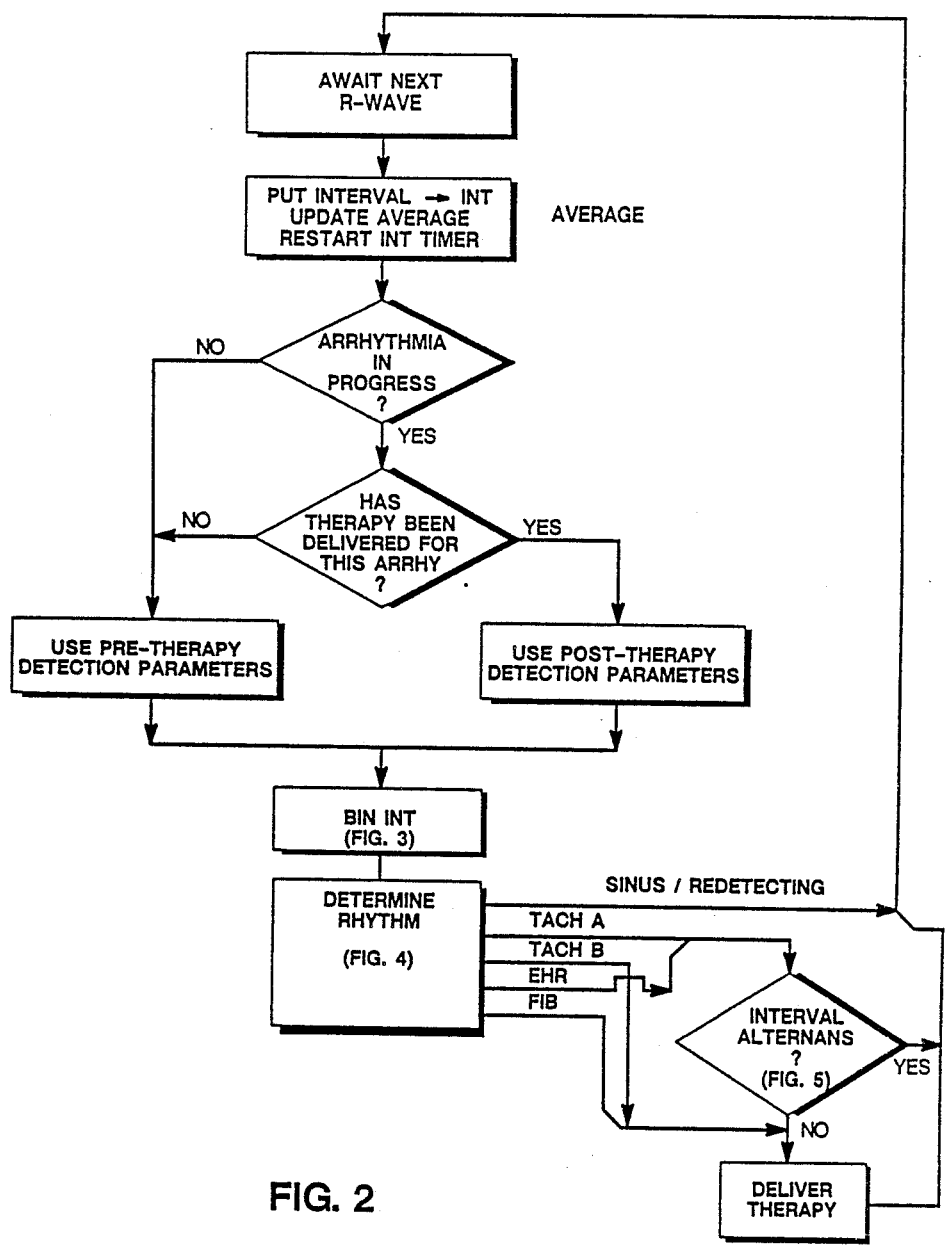
FIG. 2 is a flow chart of the arrhythmia discrimination method of the system of FIG. 1.

The method of arrhythmia discrimination of the present invention is illustrated in the flow chart of FIG. 2. The "bins" referred to therein are RAM memory locations. The basic technique is to use the average of the last four sensed events to help decide how to bin each heartbeat interval. The first bin to reach its programmed number of counts determines the diagnosis.

The following technique rapidly converges on a solution. In the event that the arrhythmia is indeterminate, it defaults to the more conservative diagnosis.

Referring to FIG. 2, the system contains a loop that starts by awaiting the next R-wave. After the R-wave is detected, the interval of the R-wave is put into a register called INT. A register called AVERAGE is updated with that interval (AVERAGE is the average of the last four intervals), and the INT timer is restarted. The system then questions whether or not the arrhythmia is in progress. If no arrhythmia is in progress, the pre-therapy detection parameters are used. If the arrhythmia is in progress and therapy has already been delivered for this arrhythmia, then the post-therapy detection parameters are used.

In this embodiment, the post-therapy detection parameter is effectively a lower rate cutoff then the pre-therapy detection parameter. Thus if a high rate tachycardia is detected, there will be continued treatment for the tachycardia notwithstanding the fact that it may revert to a lower rate tachycardia. In other words, the post-therapy detection parameters will detect what normally would have been a low rate tachycardia as if it were a high rate tachycardia. Thus even if the arrhythmia slows to the range that would previously have been a low rate tachycardia, it is considered to be a high rate tachycardia episode. In this manner, the therapies can be allowed to increase in effectiveness rather than going backwards in effectiveness.

The system then falls through to the bin interval block. At that time, the system decides whether the interval that it just received belongs in low rate tachycardia (TACH A), high rate tachycardia (TACH B), fibrillation, or the sinus bin. The bin interval block is described in more detail below with respect to FIG. 3.

The bin interval block leads to the determine rhythm block where the results of the binning exit as either having detected sinus, low rate tachycardia, high rate tachycardia, EHR (extended high rate) or having detected fibrillation.

If the system detects an arrhythmia while there is a low rate tachycardia AVERAGE, an additional check is made to see if the interval alternans inhibition is in effect. In this manner, the system looks for the case where there is a tachycardia/sinus/tachycardia/sinus, etc. sequence of events. If that is the case, the system inhibits delivering therapy and waits for the next R-wave. If that is not the case, then therapy is delivered. After delivering therapy, the system returns to waiting for the next R-wave.

The "determine rhythm" block is described in more detail with respect to FIG. 4, and the interval alternans block is described in more detail below with respect to FIG. 5, described below.

In summary with respect to the discrimination flow chart of FIG. 2, the patient's R-waves are sensed and put into an interval storage register labeled INT. There is a short term averaging of the intervals (in this preferred embodiment the last four intervals are averaged, although a fewer or greater number could be used). Depending upon the average interval, it can then be determined into which bin the interval should be put.

Figure 3:
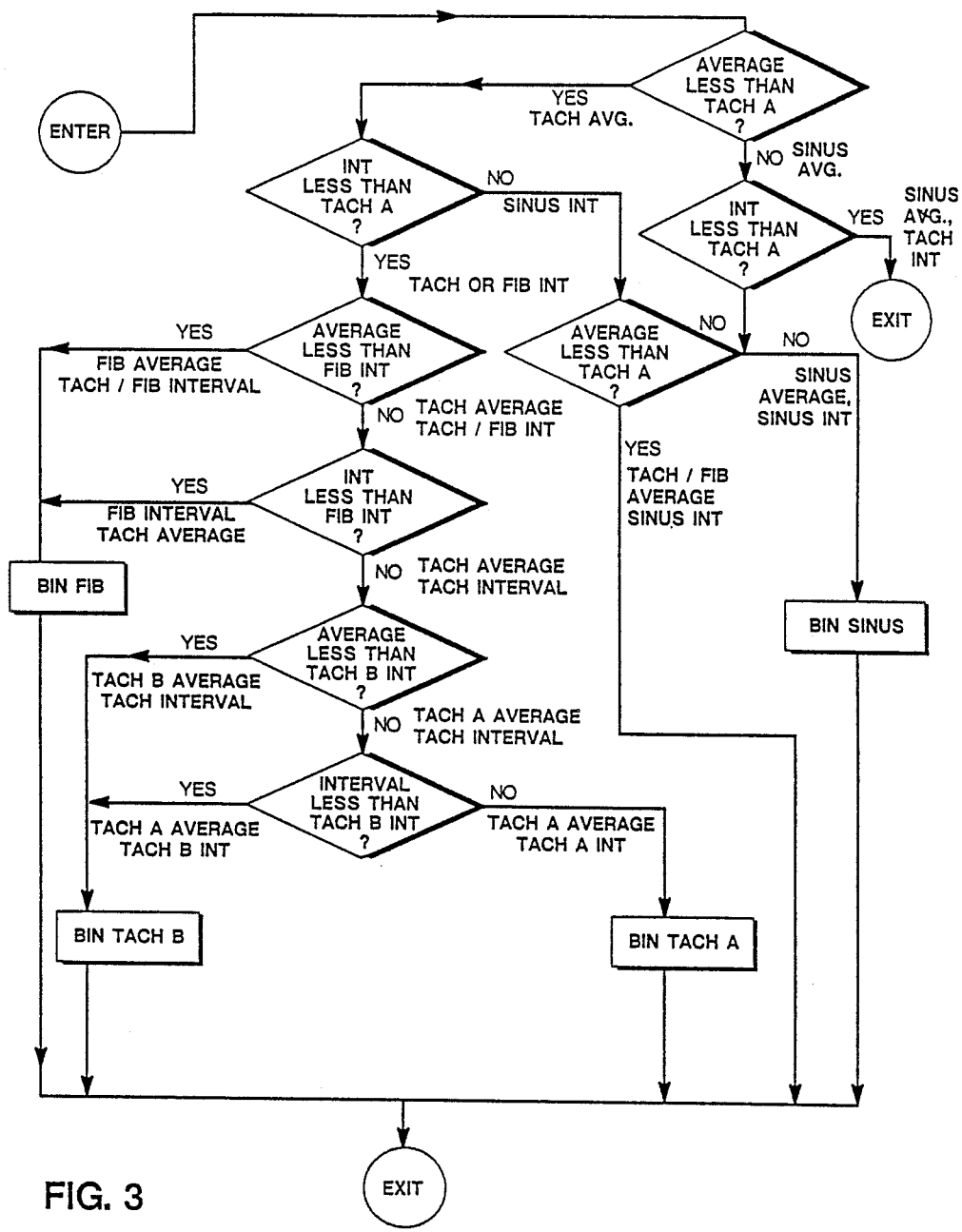
FIG. 3 is a flow chart of the bin interval block from the flow chart of FIG. 2.

Now referring to the bin interval flow chart of FIG. 3, the flow chart is entered from the detection hysteresis part of the flow chart of FIG. 2, where the system determines whether to use pre-therapy detection parameters or the post-therapy detection parameters. Those parameters are the rates at which the system detects the tachycardia and the number of intervals required for detecting tachycardia. The number of intervals required is the depth of the bin. The system first checks to see if the average interval (AVERAGE) is longer or shorter than TACH A. If it is longer than TACH A, then there is a sinus average (note that a separate programmable interval could be used as a sinus interval criterion, but in the preferred embodiment the TACH A criterion is used). If the interval is a tachyarrhythmia interval, and there is a sinus AVERAGE, no bin is incremented. If there is a sinus AVERAGE, and there is a sinus interval then a sinus interval is binned. If the AVERAGE is shorter than TACH A, then a tachyarrhythmia may be diagnosed.

Next, the system checks whether the interval is shorter than low rate tachycardia (TACH A). If it is shorter, then the interval is either a tachycardia or fibrillation interval. If the interval is longer than low rate tachycardia (TACH A), then it is a sinus interval and the system exits.

If the interval is shorter than TACH A, the average interval (AVERAGE) is checked to see if it is shorter than a low rate tachycardia. If it is not, there is a sinus average and a sinus interval and the system bins one sinus count. If the average is less than a low rate tachycardia, that means the patient has a tachycardia or fibrillation average, but since the system detected a sinus interval, nothing is binned. The system just falls through to the exit.

If, at the first decision block, the system determines that the interval is less than TACH A, then the patient has a tachycardia or a fibrillation interval and the system checks to see whether AVERAGE is less than the fibrillation requirement. If AVERAGE is less than the fibrillation criterion, the system bins a fibrillation interval. Thus whether it is a TACH interval or a TACH A or a TACH B interval, the fact that AVERAGE is fibrillation means that the system will go ahead and bin it as a fibrillation interval.

If, on the second decision block through the main decision block tree, the system determines that AVERAGE is not less than the fibrillation interval, that would mean that AVERAGE is a tachycardia average since the system has already determined that it is not a fibrillation average, but the interval may either be a tachycardia interval or a fibrillation interval. The system then checks to see whether the interval is less than the fibrillation interval requirement. If it is, the system bins the interval as a fibrillation interval. If not, then the system is at the point where it recognizes that the patient has a tachycardia average and a tachycardia interval. The system then has to determine whether it is a low rate tachycardia or a high rate tachycardia. To this end, the system checks to see if the average is less than the high rate tachycardia interval. If it is, then the patient has a high rate tachycardia average and it is binned as a TACH B. If not, the patient has a low rate tachycardia average, and the system has to check to see if the interval is less than the TACH B interval. If it is, then it is binned as a TACH B interval. If it is not, then it is binned as a TACH A interval and exits.

It can be seen that, with respect to the bin interval system, the average interval (AVERAGE) is used to determine where to bin the interval. In addition, the system checks to determine whether the interval represents sinus, TACH A, TACH B or fibrillation. As different intervals are detected, the decision blocks place the interval data into different bins depending on the interval determination using AVERAGE. Until a bin is full, the system has not decided what the arrhythmia is. Once the bin is filled, the system then diagnosis sinus rhythm or an arrhythmia and treats for that particular arrhythmia in response to the filled bin.

In a specific example, the values that the microprocessor uses to implement arrhythmia detection are as follows. These are fixed values that can be adjusted to change the arrhythmia detection for individual patients. The ranges and nominal values are shown for information only.

| | |
|---|---|
| TACH A INT | Intervals between this and TACH B INT are used to diagnose TACH A. Intervals longer than this are considered sinus; 450 msec. |
| TACH B INT | Intervals between this and FIB INT are used to diagnose TACH B; 380 msec. |
| FIB INT | Intervals shorter than this are used to diagnose fibrillation; 310 msec. |
| NUM SINUS | The number of intervals for sinus detection; 3. |
| NUM TACH A | The number of intervals for TACH A detection; 8. |
| NUM TACH B | The number of intervals for TACH B detection; 8. |
| NUM FIB | The number of intervals for fib detection; 12. |

The microprocessor maintains the following registers:

| | |
|---|---|
| AVERAGE | The average of the last four intervals. |
| SINUS CNT | The number of sinus intervals detected. |
| TACH A CNT | The number of TACH A intervals detected. |
| TACH B CNT | The number of TACH B intervals detected. |
| FIB CNT | The number of fib intervals detected. |
| TS RATIO | Used to avoid detecting a rhythm with interval alternans as an arrhythmia. |

AVERAGE is the average of the last four ECG intervals and is updated by the microprocessor every interval. Every interval is compared against AVERAGE. The intervals are binned by the microprocessor according to the following conditions:

| | |
|---|---|
| If | Interval > TACH A INT |
| and | AVERAGE > TACH A INT |
| then | Increment SINUS CNT |
| If | Interval > TACH A INT |
| and | AVERAGE < TACH A INT |
| then | No bin is incremented |
| If | TACH A INT > Interval > TACH B INT |
| and | TACH A > AVERAGE > TACH B INT |
| then | Increment TACH A CNT |
| If | TACH A INT > Interval > TACH B INT |
| and | TACH B INT > Average > FIB INT |
| then | Increment TACH B CNT |
| If | TACH A INT > Interval > TACH B INT |
| and | AVERAGE < FIB INT |
| then | Increment FIB CNT |
| If | TACH B INT > Interval > FIB INT |
| and | TACH A > AVERAGE > FIB INT |
| then | Increment TACH B CNT |
| If | TACH B INT > Interval > FIB INT |
| and | AVERAGE < FIB INT |
| then | Increment FIB CNT |
| If | Interval < FIB INT |
| and | TACH A > AVERAGE |
| then | Increment FIB CNT |

The microprocessor increments the appropriate bin after every detected ECG Interval. The first bin to count up to its respective limit causes that arrhythmia, or sinus rhythm, to be diagnosed. Upon each diagnosis, the arrhythmia detection bins are initialized.

In the operation of the system, if the system sees mixed TACH A and TACH B intervals is AVERAGE is TACH B, all the intervals are binned as TACH B. Therefore, if there is a high rate tachycardia average, the presence of some slow intervals will not cause the system to delay deciding on an arrhythmia diagnosis; the arrhythmia interval will still be binned the same as if they were the faster arrhythmia. If there is a fibrillation average, then any TACH interval gets binned as a fibrillation. If the system detects a TACH B average, then any TACH A interval gets binned as a TACH B. In this manner, the system defaults to the most conservative diagnosis. For example, if the average is TACH B and a fibrillation interval is detected, the system will bin a fibrillation interval rather than a TACH B interval in order to be as conservative as possible. In summary, the system always tends to bin diagnose the more serious arrhythmia.

Figure 4:
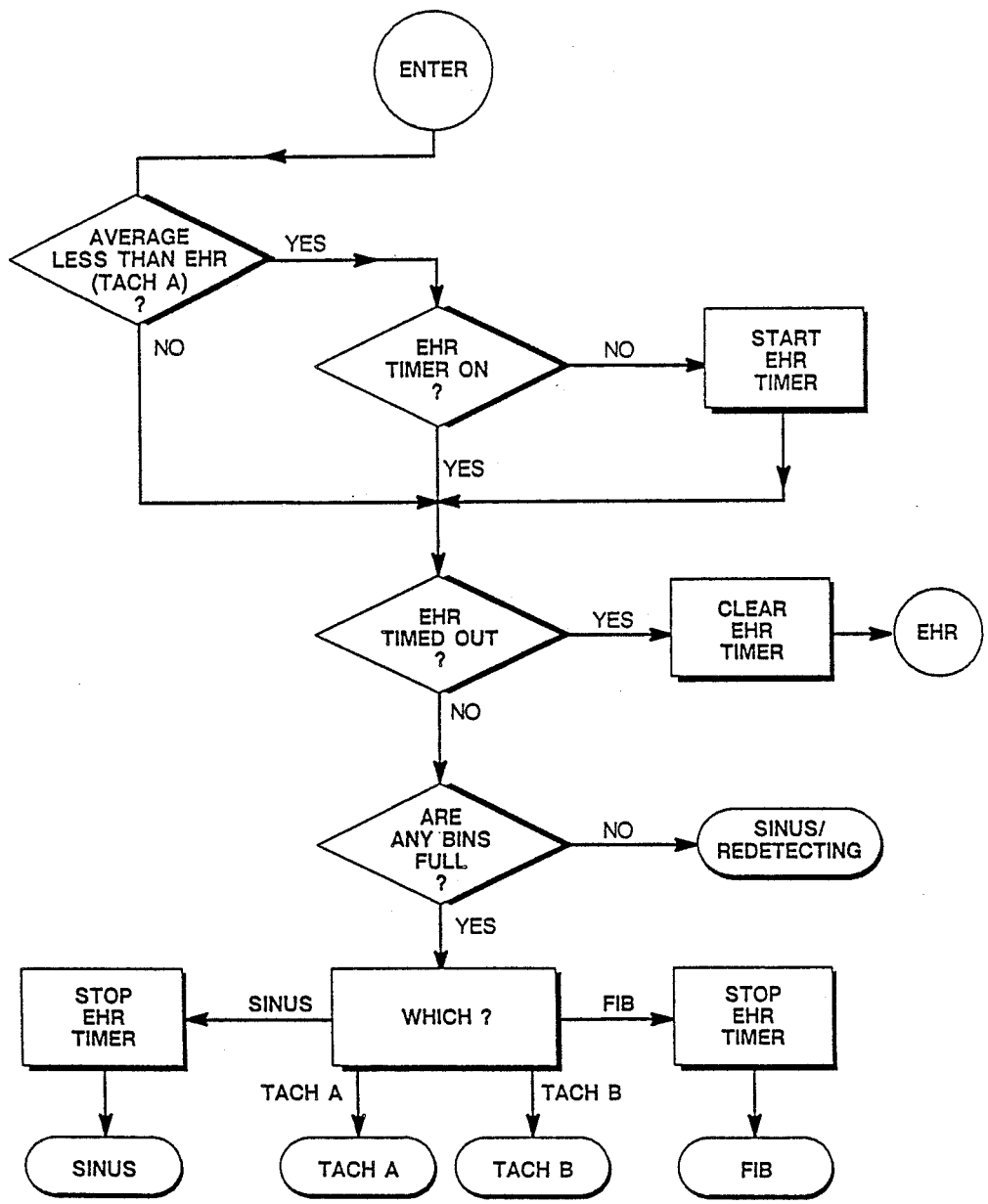
FIG. 4 is a flow chart of the determine rhythm block from the flow chart of FIG. 2.
Figure 5:
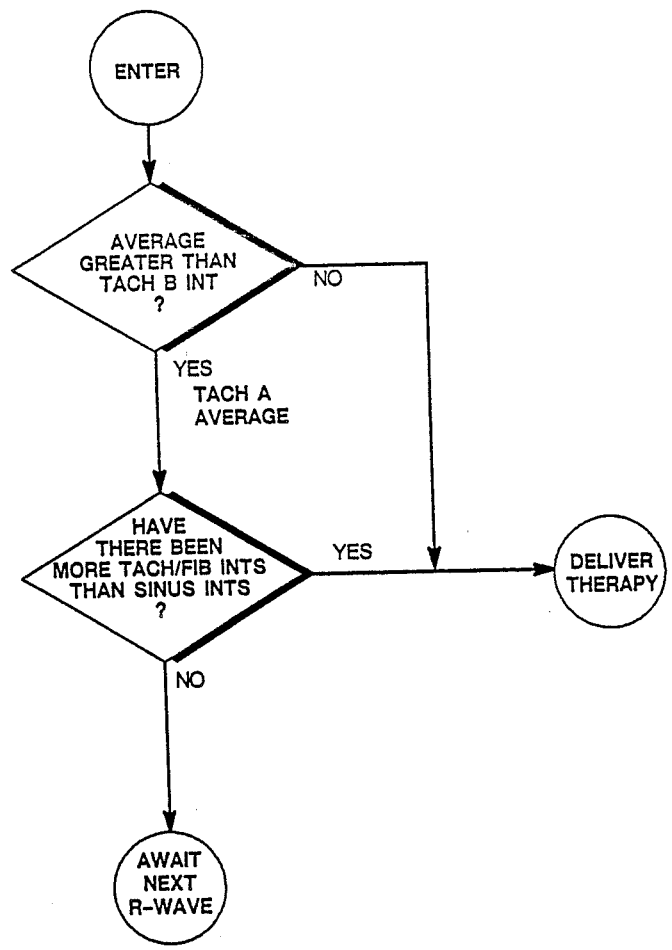
FIG. 5 is a flow chart of the interval alternans diamond from the flow chart of FIG. 2.

The following is a discussion of the determine rhythm flow chart of FIG. 4. Referring to FIG. 4, once the interval has been placed into a bin, the system must determine whether an arrhythmia has been detected. In effect, the system is determining whether a bin is full. However, the system must first go through and see if the AVERAGE is less than the EHR detection interval (in this embodiment TACH A is used as the EHR detection interval, though generally it can be a separately programmable rate criterion). If it is, then the system checks to see if the EHR timer is already running. If it isn't, that means that the patient has gone from either sinus to the beginning of a tachycardia or there has been a defibrillation therapy but there is still a tachycardia in progress. If either one of those are true, then the extended high rate (EHR) timer is started. If the EHR timer has been ongoing, the system just falls through and checks to see if the EHR timer has timed out. If it has, the EHR timer is cleared and the diagnosis is that EHR is the arrhythmia that has been detected.

If the EHR timer has not timed out, the system falls through and checks to see if any of the bins are full. If none of the bins is full, the system is either redetecting sinus or is redetecting one of the arrhythmias; the system goes to the sinus/redetecting exit. If a bin is full, since only one bin will be full at this time, the system checks to see which bin is filled and then clears all of the bins.

If the system detects that either a sinus bin is full or a fibrillation bin is full, then the EHR timer is cleared and the diagnosis is either sinus or fibrillation, respectively. If the system determines either a TACH A or a TACH B, the EHR timer is not cleared and the diagnosis is TACH A or TACH B, respectively. The depth of a bin is determined in memory by how the device is programmed. Thus, each bin is a RAM location that is counting up to a value that is determined by another RAM location that is under programmer control. The physician can select the particular interval that is used to determine whether or not a give cardiac interval can be classed as a TACH A, a TACH B or a fib interval. It is those programmable parameters, i.e., the interval cutoff and the depth of the bin, that are used in the implementation of detection hysteresis. Thus there are two parameters per arrhythmia in this embodiment.

Typical examples for those parameters are set forth above. For example, TACH A may be set at 450 msec., TACH B at 380 msec., and fibrillation at 310 msec. Thus, if the system detects an interval that is between 450 msec. and 380 msec., it would be binned as a TACH A interval if the average were also TACH A. If the interval were between 380 msec. and 310 msec., it is a TACH B interval if the average is TACH B or TACH A. If the interval is shorter than 310 msec., then it is binned as a fibrillation interval (as long as AVERAGE is shorter than TACH A; if it is not, then no interval is binned). If the interval is longer than 450 msec., then it is a sinus interval. The number of intervals required for each diagnosis may be 3 to detect sinus, 8 to detect TACH A, 8 to detect TACH B and 12 to detect fibrillation. This means that the fibrillation bin is 12 deep, the sinus bin is 3 deep, etc. The bins, however, can be programmable up to 255 intervals but the previous numbers are being given as specific examples.

As a further explanation of the extended high rate (EHR) system, as soon as the average goes from being a sinus average to a EHR average (TACH A in this example), the EHR timer is started. Then, if the EHR timer times out at any time, whether the bins are full or not, that determines that the system has detected EHR. EHR is another way to start fibrillation or some other programmed therapy. If the system detects sinus at any time, or if it detects fibrillation or EHR at any time, the EHR timer is cleared.

The following is an example of what will happen if any arrhythmia starts the EHR timer. If the arrhythmia does not persist, and sinus rhythm is detected, then the EHR timer is cleared until another arrhythmia starts. The arrhythmia starts, TACH A is detected, some TACH A therapy is given, and possibly TACH B is detected and some TACH B therapy is given. The EHR timer then times out, and the system will abandon the TACH A or TACH B therapy and will revert to fibrillation therapy. In other words, it is basically a safety exit to prevent the patient from being engaged in less effective therapies for a long time.

The interval alternans flow chart of FIG. 5 will now be discussed.

The interval alternans section is entered from the determine rhythm block. The average is checked to see if it is greater than or a TACH B average. If it is not greater than TACH B, then the rhythm is rapid. Thus it is either a TACH B average or a fibrillation average and in that case therapy is delivered whether or not there is an interval alternans.

If, however, the average is greater than a TACH B interval, that means that the patient has a TACH A average and then a further check is made to see whether there have been more TACH intervals than sinus intervals during the detection period. If there have not, then the system determines that it is not an arrhythmia and awaits the next R-wave. If there have been more TACH or fibrillation intervals than sinus intervals, the system continues on to deliver the therapy. The reason for this is that if there is a bigeminal rhythm, the average rate might be a TACH A rate but the patient is not in arrhythmia and it is desirable to avoid treating the patient, even though the short intervals may be TACH B intervals or fibrillation intervals. This interval alternans program provides a means to avoid treating a bigeminal rhythm.

A novel system for cardiac therapy has been shown and described. By means of the present invention, the system can rapidly converge to a solution and in the event that the arrhythmia is indeterminate, there is a default to the most conservative diagnosis. By using a novel method of binning, the system allows the use of a higher arrhythmia detection rate in a tiered defibrillator, without the disadvantage of failing to terminate slower arrhythmias that might result from the therapy. The invention also allows the system to keep track of the ratio of sinus intervals to tachycardia intervals, and to require more tachycardia intervals than sinus intervals so that a bigeminal rhythm will not be detected as a tachycardia.

Although a detailed explanation of the invention has been shown and described, it is to be understood that various modifications and substitutions may be made by those skilled in the art without departing from the novel spirit and scope of the present invention. In particular, incrementing as herein used is meant to include counting up to a preset limit, or counting down from the limit, or any other manner of maintaining bins electronically.

What is claimed is:

1. A cardiac therapy method using an implanted cardiac pulse generator, which comprises the steps of:
    sensing a patient's heartbeat;
    providing storage means including a plurality of storage count bins, including a sinus bin, a tachycardia bin, and a fibrillation bin;
    determining the intervals between heartbeats;
    if the determined interval is within a sinus band, then changing the count of the sinus bin;
    if the determined interval is within a tachycardia band, then changing the count of the tachycardia bin;
    if the determined interval is within a fibrillation band, then changing the count of the fibrillation bin;
    assigning a count limit to each bin;
    detecting when the first bin reaches its count limit;
    providing a diagnosis of the patient's cardiac rhythm that is responsive to the first bin to reach its count limit; and
    initializing said storage bins.

2. A method as defined by claim 1, wherein the step of providing a tachycardia bin includes the step of providing a low rate tachycardia bin and a high rate tachycardia bin.

3. A method as defined by claim 1, wherein the step of assigning the count limit to each bin includes the step of assigning different count limits to different bins.

4. A method as defined by claim 1, wherein the step of determining the intervals between heartbeats includes the step of averaging a predetermined number of sensed heartbeats to provide an average interval.

5. A method as defined by claim 4, wherein the step of determining the intervals between heartbeats further includes the step of comparing each sensed interval against the average and selecting the band in response to this comparison.

6. A method as defined by claim 5, including the step of updating the average with sensed intervals.

7. A cardiac therapy method using an implanted cardiac pulse generator, which comprises the steps of:
sensing a patient's heartbeat;
providing storage means including a plurality of storage count bins, including a sinus bin, a tachycardia bin, and a fibrillation bin;
determining the intervals between heartbeats;
if the determined interval is within a sinus band, then changing the count of the sinus bin;
if the determined interval is within a tachycardia band, then changing the count of the tachycardia bin;
if the determined interval is within a fibrillation band, then changing the count of the fibrillation bin;
assigning a count limit to each bin including the step of assigning different count limits to different bins, wherein the count limit for tachycardia diagnosis is different than the count limit for sinus;
detecting when the first bin reaches its count limit;
providing a diagnosis of the patient's cardiac rhythm that is responsive to the first bin to reach its count limit; and initializing said storage bins.

8. A method as defined by claim 7, wherein the step of providing a tachycardia bin includes the step of providing a low rate tachycardia bin and a high rate tachycardia bin.

9. A cardiac therapy method using an implanted cardiac pulse generator, which comprises the steps of:
sensing a patient's heartbeat;
providing storage count means including a plurality of storage bins, each of which corresponds to a different cardiac rhythm band;
determining the intervals between heartbeats; changing the count of the storage bin corresponding to the cardiac rhythm band of the determined heartbeat interval;
assigning a count limit to each storage bin;
detecting when the first bin reaches its count limit;
providing a diagnosis of the patient's cardiac rhythm that is responsive to the first bin to reach its count limit; and
initializing said storage bins.

10. A method as described in claim 9, wherein the step of providing storage means comprises the step of providing a sinus storage bin, a tachycardia storage bin and a fibrillation storage bin.

11. A method as defined by claim 10, wherein the step of providing a tachycardia bin includes the step of providing a low rate tachycardia bin and a high rate tachycardia bin.

12. A method as defined by claim 9, wherein the step of assigning a count limit to each bin includes the step of assigning different count limits to different bins.

13. A method as defined by claim 9, wherein the step of determining the intervals between heartbeats includes the step of averaging a predetermined number of sensed heartbeats to provide an average interval, and further includes the step of comparing each sensed interval against the average and selecting the band in response to this comparison; and updating the average with sensed intervals.

14. A cardiac therapy method using an implanted cardiac pulse generator, which comprises the steps of:
sensing a patient's heatbeat;
determining the intervals between heartbeats;
determining the ratio of sinus intervals to arrhythmia intervals; and
treating for arrhythmia only if the number of arrhythmia intervals exceed the number of sinus intervals notwithstanding that the average of the sinus and arrhythmia intervals is shorter than sinus rhythm.

15. A cardiac therapy method using an implanted cardiac pulse generator, which comprises the steps of:
sensing a patient's heartbeat;
determining the intervals between heartbeats;
averaging a predetermined number of heartbeats;
tracking the ratio of sinus intervals to tachycardia intervals;
if there are more sinus intervals than tachycardia intervals, then not treating for tachycardia; and
if there are more tachycardia intervals than sinus intervals, then treating for tachycardia.

16. A cardiac therapy method using an implanted cardiac pulse generator, which comprises the steps of:
sensing a patient's heartbeat;
providing storage means including a plurality of storage count bins, each of which corresponds to a different cardiac rhythm band;
determining the intervals between heartbeats; changing the count of the storage bin corresponding to the cardiac rhythm band of the determined heartbeat interval;
assigning a count limit to each storage bin;
detecting when the first bin reaches its count limit;
providing a diagnosis of the patient's cardiac rhythm that is responsive to the first bin to reach its count limit;
if an arrhythmia is detected, then tracking the ratio of sinus intervals to arrhythmia intervals;
if there are more sinus intervals than arrhythmia intervals, then not treating for an arrhythmia; but,
if there are more arrhythmia intervals than sinus intervals, then treating for the arrhythmia.

17. A cardiac therapy method using an implanted cardiac pulse generator, which comprises the steps of:
sensing a patient's heartbeat;
averaging a predetermined number of sensed heartbeats to provide an average interval;
providing storage means including a plurality of storage count bins, including a sinus bin, a low rate tachycardia bin, a high rate tachycardia bin, and fibrillation bin;
if the average interval is within a sinus band, then changing the count of the sinus bin;
if the average interval is within a low rate tachycardia band, then changing the count of the low rate tachycardia bin;
if the average interval is within the high rate tachycardia band, then changing the count of the high rate tachycardia bin;
if the average interval is within a fibrillation band, then changing the count of the fibrillation bin;
assigning a count limit to each bin;
detecting when the first bin reaches its count limit;
providing a diagnosis of the patient's cardiac rhythm that is responsive to the first bin to reach its count limit;

if a low rate tachycardia bin is the first bin to reach its count limit, then determining if the average interval is greater than the high rate tachycardia interval; and if the average interval is not greater than the high rate tachycardia interval, then delivering a high energy shock to the heart.

18. A method as defined by claim 17, wherein if the average interval is greater than the high rate tachycardia interval, then tracking the ratio of sinus intervals to tachycardia intervals;

if there are more sinus intervals than tachycardia intervals, then not treating for tachycardia; and if there are more tachycardia intervals than sinus intervals, then treating for tachycardia.

19. A cardiac therapy system which comprises:
an implanted cardiac pulse generator having means for sensing a patient's heartbeat;
storage means including a plurality of storage count bins, including a sinus bin, a tachycardia bin, and a fibrillation bin;
means for determining the intervals between heartbeats;
means for changing the count of the sinus bin if the determined interval is within a sinus band;
means for changing the count of the tachycardia bin if the determined interval is within a tachycardia band;
means for changing the count of the fibrillation bin if the determined interval is within a fibrillation band;
means for assigning a count limit to each bin;
means for detecting when the first bin reaches its count limit;
means for providing a diagnosis of the patient's cardiac rhythm that is responsive to the first bin to reach its count limit; and
means for initializing said temporary storage bins.

20. A cardiac therapy system which comprises:
an implanted cardiac pulse generator having means for sensing a patient's heartbeat;
storage means including a plurality of storage count bins, each of which corresponds to a different cardiac rhythm band;
means for determining the intervals between heartbeats;
means for changing the count of the storage bin corresponding to the cardiac rhythm band of the determined heartbeat interval;
means for assigning a count limit to each storage bin;
means for detecting when the first bin reaches its count limit;
means for providing a diagnosis of the patient's cardiac rhythm that is responsive to the first bin to reach its count limit; and
means for intializing said storage bins.

21. A cardiac therapy system which comprises:
an implanted cardiac pulse generator having means for sensing a patient's heartbeat;
means for determining the intervals between heartbeats;
means for averaging a predetermined number of heartbeats;
means for tracking the ratio of sinus intervals to tachycardia intervals; and
means for treating for tachycardia if there are more tachycardia intervals than sinus intervals but not treating for tachycardia if there are more sinus intervals than tachycardia intervals.

* * * * *